(12) United States Patent
Cropper et al.

(10) Patent No.: US 8,435,174 B2
(45) Date of Patent: May 7, 2013

(54) METHODS AND DEVICES FOR ACCESSING A BODY CAVITY

(75) Inventors: Michael S. Cropper, Edgewood, KY (US); Salvatore G. Caldarise, Belle Mead, NJ (US); Patrick M. Schleitweiler, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 639 days.

(21) Appl. No.: 12/635,990

(22) Filed: Dec. 11, 2009

(65) Prior Publication Data
US 2011/0144440 A1 Jun. 16, 2011

(51) Int. Cl.
*A61B 1/32* (2006.01)
(52) U.S. Cl.
USPC .......................................... 600/203
(58) Field of Classification Search ........... 600/203, 600/204, 206
See application file for complete search history.

(56) References Cited

U.S. PATENT DOCUMENTS

| | | |
|---|---|---|
| 3,397,699 A | 8/1968 | Kohl |
| 4,022,191 A | 5/1977 | Jamshidi |
| 4,608,977 A | 9/1986 | Brown |
| 4,809,694 A | 3/1989 | Ferrara |
| 5,031,634 A | 7/1991 | Simon |
| 5,053,042 A | 10/1991 | Bidwell |
| 5,100,387 A | 3/1992 | Ng |
| 5,201,742 A | 4/1993 | Hasson |
| 5,235,987 A | 8/1993 | Wolfe |
| 5,312,417 A | 5/1994 | Wilk |
| 5,316,014 A | 5/1994 | Livingston |
| 5,320,111 A | 6/1994 | Livingston |
| 5,330,437 A | 7/1994 | Durman |
| 5,330,497 A * | 7/1994 | Freitas et al. .................. 606/185 |
| 5,342,315 A | 8/1994 | Rowe et al. |
| 5,431,676 A | 7/1995 | Dubrul et al. |
| 5,494,039 A | 2/1996 | Onik et al. |
| 5,496,289 A * | 3/1996 | Wenstrom, Jr. ................ 604/264 |

(Continued)

FOREIGN PATENT DOCUMENTS

| | | |
|---|---|---|
| EP | 577400 A1 | 1/1994 |
| EP | 1623693 | 2/2006 |

(Continued)

OTHER PUBLICATIONS

U.S. Appl. No. 12/339,473, filed Mar. 6, 2009, Methods and Devices for Providing Access Into a Body Cavity.

(Continued)

*Primary Examiner* — Nicholas Woodall
(74) *Attorney, Agent, or Firm* — Nutter McClennen & Fish LLP

(57) ABSTRACT

Methods and devices are provided for accessing a surgical site. In one embodiment, an access device is provided having a housing and a cannula extending distally therefrom. The cannula and the housing can define a working channel extending longitudinally therethrough. The cannula can be movable between an insertion configuration and a deployed configuration. The access device can also include an obturator insertable through the working channel. In one embodiment, the obturator can be configured to selectively mate with the cannula such that rotation of the obturator is effective to cause corresponding rotation of the cannula. In another embodiment, the obturator can be configured to move the cannula from the insertion configuration to the deployed configuration when the obturator is fully disposed within the cannula.

19 Claims, 8 Drawing Sheets

U.S. PATENT DOCUMENTS

| | | | |
|---|---|---|---|
| 5,569,205 A | 10/1996 | Hart et al. |
| 5,628,732 A | 5/1997 | Antoon, Jr. et al. |
| 5,647,373 A | 7/1997 | Paltieli et al. |
| 5,707,359 A | 1/1998 | Bufalini |
| 5,857,999 A | 1/1999 | Quick et al. |
| 5,868,673 A | 2/1999 | Vesely |
| 5,882,340 A | 3/1999 | Yoon |
| 5,911,707 A | 6/1999 | Wolvek et al. |
| 5,916,175 A | 6/1999 | Bauer et al. |
| 5,941,889 A | 8/1999 | Cermak |
| 5,954,670 A | 9/1999 | Baker |
| 5,984,930 A | 11/1999 | Maciunas et al. |
| 6,017,356 A | 1/2000 | Frederick et al. |
| D422,706 S | 4/2000 | Bucholz et al. |
| 6,048,321 A | 4/2000 | McPherson et al. |
| 6,110,182 A | 8/2000 | Mowlai-Ashtiani |
| 6,162,196 A | 12/2000 | Hart et al. |
| 6,195,577 B1 | 2/2001 | Truwit et al. |
| 6,203,499 B1 | 3/2001 | Imling |
| 6,216,029 B1 | 4/2001 | Paltieli et al. |
| 6,231,565 B1 | 5/2001 | Tovey et al. |
| 6,231,585 B1 | 5/2001 | Takahashi et al. |
| 6,236,875 B1 | 5/2001 | Bucholz et al. |
| 6,245,028 B1 | 6/2001 | Furst et al. |
| 6,283,942 B1 | 9/2001 | Staehlin et al. |
| 6,361,499 B1 | 3/2002 | Bates et al. |
| 6,379,307 B1 | 4/2002 | Filly et al. |
| 6,400,979 B1 | 6/2002 | Stoianovici et al. |
| 6,443,960 B1 | 9/2002 | Brabrand et al. |
| 6,445,943 B1 | 9/2002 | Ferre et al. |
| 6,468,226 B1 | 10/2002 | McIntyre, IV |
| 6,475,152 B1 | 11/2002 | Kelly, Jr. et al. |
| 6,490,467 B1 | 12/2002 | Bucholz et al. |
| 6,501,981 B1 | 12/2002 | Schweikard et al. |
| 6,529,765 B1 | 3/2003 | Franck et al. |
| 6,535,756 B1 | 3/2003 | Simon et al. |
| 6,539,121 B1 | 3/2003 | Haskell et al. |
| 6,546,279 B1 | 4/2003 | Bova et al. |
| 6,547,786 B1 | 4/2003 | Goble |
| 6,551,270 B1 | 4/2003 | Bimbo et al. |
| 6,665,554 B1 | 12/2003 | Charles et al. |
| 6,687,531 B1 | 2/2004 | Ferre et al. |
| 6,723,106 B1 | 4/2004 | Charles et al. |
| 6,731,966 B1 | 5/2004 | Spigelman et al. |
| 6,752,812 B1 | 6/2004 | Truwit |
| 6,770,027 B2 | 8/2004 | Banik et al. |
| 6,782,288 B2 | 8/2004 | Truwit |
| 6,783,524 B2 | 8/2004 | Anderson |
| 6,785,572 B2 | 8/2004 | Yanof et al. |
| 6,808,492 B2 | 10/2004 | Snyder |
| 7,021,173 B2 | 4/2006 | Stoianovici et al. |
| 7,056,329 B2 | 6/2006 | Kerr |
| 7,076,106 B2 | 7/2006 | Haskell et al. |
| 7,083,626 B2 | 8/2006 | Hart et al. |
| 7,163,525 B2 | 1/2007 | Franer |
| 7,371,227 B2 | 5/2008 | Zeiner |
| 8,204,029 B2 | 6/2012 | Stephenson et al. |
| 2003/0100814 A1 | 5/2003 | Kindlein |
| 2003/0208207 A1 | 11/2003 | Layer |
| 2003/0229338 A1 | 12/2003 | Irion et al. |
| 2004/0082969 A1 | 4/2004 | Kerr |
| 2004/0185453 A1 | 9/2004 | Myerson et al. |
| 2004/0230161 A1 | 11/2004 | Zeiner |
| 2004/0254426 A1 | 12/2004 | Wenchell |
| 2005/0222582 A1 | 10/2005 | Wenchell |
| 2006/0149137 A1 | 7/2006 | Pingleton et al. |
| 2006/0247499 A1 | 11/2006 | Butler et al. |
| 2006/0247673 A1 | 11/2006 | Voegele et al. |
| 2007/0185453 A1 | 8/2007 | Michael et al. |
| 2007/0260121 A1 | 11/2007 | Bakos et al. |
| 2007/0260273 A1 | 11/2007 | Cropper et al. |
| 2008/0086080 A1 | 4/2008 | Mastri et al. |
| 2008/0086167 A1 | 4/2008 | Mastri et al. |
| 2008/0242930 A1 | 10/2008 | Hanypsiak et al. |
| 2008/0249373 A1 | 10/2008 | Wenchell |
| 2008/0255519 A1 | 10/2008 | Piskun et al. |
| 2009/0005799 A1 | 1/2009 | Franer et al. |
| 2009/0105659 A1 | 4/2009 | Bettuchi et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0118830 A1 | 5/2010 | Stephenson et al. |
| 2010/0228091 A1 | 9/2010 | Widenhouse et al. |
| 2010/0228092 A1 | 9/2010 | Ortiz et al. |
| 2010/0228096 A1 | 9/2010 | Weisenburgh, II et al. |
| 2010/0261974 A1 | 10/2010 | Shelton, IV et al. |
| 2010/0268162 A1 | 10/2010 | Shelton, IV et al. |
| 2010/0312060 A1 | 12/2010 | Widenhouse et al. |
| 2010/0312061 A1 | 12/2010 | Hess et al. |
| 2010/0312062 A1 | 12/2010 | Cropper et al. |
| 2010/0312063 A1 | 12/2010 | Hess et al. |
| 2010/0312064 A1 | 12/2010 | Weisenburgh, II et al. |
| 2010/0312189 A1 | 12/2010 | Shelton, IV et al. |
| 2011/0028793 A1 | 2/2011 | Martin et al. |
| 2011/0028794 A1 | 2/2011 | Widenhouse et al. |
| 2011/0124967 A1 | 5/2011 | Morgan et al. |
| 2011/0144437 A1 | 6/2011 | Ortiz et al. |
| 2011/0144440 A1 | 6/2011 | Cropper et al. |
| 2011/0144442 A1 | 6/2011 | Farrell et al. |
| 2011/0144443 A1 | 6/2011 | Shelton, IV et al. |
| 2011/0144444 A1 | 6/2011 | Sakai, Jr. et al. |
| 2011/0144447 A1 | 6/2011 | Schleitweiler et al. |
| 2011/0144448 A1 | 6/2011 | Shelton, IV et al. |
| 2011/0144449 A1 | 6/2011 | Ortiz et al. |
| 2011/0144589 A1 | 6/2011 | Ortiz et al. |
| 2011/0144590 A1 | 6/2011 | Sakai, Jr. et al. |

FOREIGN PATENT DOCUMENTS

| | | |
|---|---|---|
| WO | 9636283 A1 | 11/1996 |
| WO | 0041759 A1 | 7/2000 |
| WO | 0062689 A1 | 10/2000 |
| WO | 0108563 A2 | 2/2001 |
| WO | 2005097019 A2 | 10/2005 |
| WO | 2005097234 A2 | 10/2005 |
| WO | 2006057982 A2 | 6/2006 |
| WO | 2009076188 | 6/2009 |

OTHER PUBLICATIONS

U.S. Appl. No. 12/399,482, filed Mar. 6, 2009, Methods and Devices for Providing Access Into a Body Cavity.

U.S. Appl. No. 12/399,547, filed Mar. 6, 2009, Surgical Access Devices and Methods Providing Seal Movement in Predefined Paths.

U.S. Appl. No. 12/399,625, filed Mar. 6, 2009, Methods and Devices for Providing Access Into a Body Cavity.

U.S. Appl. No. 12/420,146, filed Apr. 8, 2009, Methods and Devices for Providing Access Into a Body Cavity.

U.S. Appl. No. 12/424,213, filed Apr. 15, 2009, Cannula With Sealing Elements.

U.S. Appl. No. 12/478,862, filed Jun. 5, 2009, Flexible Cannula Devices and Methods.

U.S. Appl. No. 12/478,882, filed Jun. 5, 2009, Multi-Planar Obturator With Foldable Retractor.

U.S. Appl. No. 12/479,030, filed Jun. 5, 2009, Retractor With Integrated Wound Closure.

U.S. Appl. No. 12/479,096, filed Jun. 5, 2009, Interlocking Seal Components.

U.S. Appl. No. 12/479,293, filed Jun. 5, 2009, Methods and Devices for Providing Access Through Tissue to Surgical Site.

U.S. Appl. No. 12/512,542, filed Jul. 30, 2009, Methods and Devices for Providing Access Into a Body Cavity.

U.S. Appl. No. 12/512,568, filed Jun. 30, 2009, Methods and Devices for Providing Access Into a Body Cavity.

U.S. Appl. No. 12/623,018, filed Nov. 20, 2009, Discrete Flexion Head for Single Port Device.

U.S. Appl. No. 12/635,754, filed Dec. 11, 2009, Methods and Devices for Providing Access Into a Body Cavity.

U.S. Appl. No. 12/635,762, filed Dec. 11, 2009, Methods and Devices for Providing Access Into a Body Cavity.

U.S. Appl. No. 12/636,020, filed Dec. 11, 2009, Inverted Conical Expandable Retractor.
U.S. Appl. No. 12/636,023, filed Dec. 11, 2009, Inverted Concical Expandable Retractor With Coil Spring.
U.S. Appl. No. 12/636,174, filed 12/11/09, Methods and Devices for Providing Access Through Tissue to a Surgical Site.
U.S. Appl. No. 12/636,184, filed Dec. 11, 2009, Methods and Devices for Providing Access Through Tissue to a Surgical Site.
U.S. Appl. No. 12/636,191, filed Dec. 11, 2009, Methods and Devices for Providing Access Through Tissue to a Surgical Site.
U.S. Appl. No. 12/636,205, filed Dec. 11, 2009, Methods and Devices for Providing Access Through Tissue to a Surgical Site.
U.S. Appl. No. 12/636,232, filed Dec. 11, 2009, Methods and Devices for Providing Access Through Tissue to a Surgical Site.
U.S. Appl. No. 12/479,395, filed Jun. 5, 2009, Methods and Devices for Accessing a Body Cavity Using Surgical Access Device With Modular Seal Components.
International Search Report, PCT/US2010/059633, Mar. 24, 2011.

* cited by examiner

METHODS AND DEVICES FOR ACCESSING A BODY CAVITY

FIELD OF THE INVENTION

The present invention relates to methods and devices for accessing a surgical site.

BACKGROUND OF THE INVENTION

Access ports are widely used in medical procedures to gain access to anatomical cavities ranging in size from the abdomen to small blood vessels, such as veins and arteries, epidural, pleural and subarachnoid spaces, heart ventricles, and spinal and synovial cavities. The use of access ports has become common as they provide minimally invasive techniques for establishing a portal for a number of procedures, such as those involving the abdominal cavity. Reduced postoperative recovery time, markedly decreased post-operative pain and wound infection, and improved cosmetic outcome are well established benefits of minimally invasive surgery, derived mainly from the ability of surgeons to perform an operation utilizing smaller incisions of the body cavity wall.

A trocar is one type of access port that is commonly used to provide a minimally invasive pathway for accessing a surgical site. Trocars generally include a cutting assembly or obturator that is disposed within an outer cannula. The sharp distal end of the cutting assembly, with the cannula disposed therearound, is urged through the skin until it enters the anatomical cavity being penetrated. Because the umbilicus is well-hidden and the thinnest and least vascularized area of the abdominal wall, the umbilicus is generally a preferred choice of abdominal cavity entry in laparoscopic procedures. Further, an umbilical incision can be easily enlarged (in order to eviscerate a larger specimen) without significantly compromising cosmesis and without increasing the chances of wound complications. The abdominal cavity is typically insufflated with $CO_2$ gas to a pressure of around 15 mm Hg. The cutting assembly is then withdrawn from the cannula, which remains in place to provide a passageway through which access to the anatomical cavity is provided for other surgical devices, e.g., laparoscopic instruments such as graspers, dissectors, scissors, retractors, etc.

One drawback of current trocars is that they inhibit movement of surgical instruments inserted therethrough, due to the long, rigid, and narrow lumen defined therein. As a result, a surgeon must tilt the entire rigid access device in order manipulate the instruments, while avoiding damage to non-target organs of the abdominal cavity. Further, such devices can be accidentally moved and/or removed during surgery, which could affect insufflation as well as interfere with proper positioning of the instruments.

Accordingly, there remains a need for improved instruments and trocar systems.

SUMMARY OF THE INVENTION

The present invention generally provides methods and devices for surgically accessing a body cavity. In one exemplary embodiment, a surgical access device is provided. The access device can include a housing and a cannula extending distally therefrom. The cannula and the housing can define a working channel extending longitudinally therethrough. The cannula can be movable between an insertion configuration and a deployed configuration, and the cannula can include a distal anchoring element having a maximum outer diameter in the deployed configuration that is greater than a maximum outer diameter of the cannula in the insertion configuration. The access device can also include an obturator insertable through the working channel. The obturator can have an engagement feature configured to mate with a complementary engagement feature formed on the cannula such that rotation of the obturator is effective to cause corresponding rotation of the cannula.

In one embodiment, the obturator can be configured to move proximally relative to a proximal end of the cannula when the engagement features are engaged to move the cannula from the insertion configuration to the deployed configuration. Axial movement of the obturator within the cannula, for example, can be effective to change a distance between the distal end of the cannula and a proximal end of the cannula.

The engagement features can be formed, for example, on a distal end of the obturator and cannula. In one exemplary embodiment, rotation of the obturator relative to the cannula can be effective to cause the engagement features to engage with and disengage from one another. In one embodiment, the engagement features can be a protrusion extending from one of the cannula and the obturator and an opening formed in another one of the cannula and the obturator. The opening can be configured to receive the protrusion.

In another exemplary embodiment, the surgical access device can include an actuation mechanism formed on the obturator. The actuation mechanism can be effective to change a length of the obturator extending distal to the housing, wherein changing the length of the obturator can be effective to move the cannula between the insertion configuration and the deployed configuration.

In one exemplary embodiment, the cannula can include an elastically deformable and extendible outer sheath and first and second telescoping inner tubes.

The access device can also include other features, such as at least one seal element disposed within the working channel. The seal element can be configured to form at least one of a seal around an instrument disposed through the working channel and a seal across the working channel when no instrument is disposed therethrough.

In another exemplary embodiment, a surgical access device is provided and includes a housing and a cannula extending distally from the housing. The cannula and the housing can define a working channel extending therethrough. The cannula can include an expandable anchor formed on a distal portion thereof. The access device can also include an obturator disposable within the working channel and a rotatable actuation mechanism operatively associated with the obturator. The rotatable actuation mechanism can be effective to expand the expandable anchor on the distal portion of the cannula when the obturator is fully disposed within the cannula such that a distal tip of the obturator extends beyond a distal end of the cannula.

In one embodiment, the rotatable actuation mechanism can be a rotatable knob coupled to the obturator. The rotatable knob can be effective to rotate to change a length of the obturator extending distal to the housing. In one embodiment, the obturator can include inner and outer tubes that are axially movable relative to one another. Rotation of the rotatable knob can be effective to move the inner tube relative to the outer tube. In one embodiment, one of the inner and outer tubes can include a guide channel formed therein, and the other one of the inner and outer tubes can include a detent formed therein. The detent can be, for example, slidably disposed within the guide channel. In one embodiment, the guide channel and detent can cause axial movement of the inner tube relative to the outer tube upon rotation of the rotatable knob. In another embodiment, a distal end of the inner tube can be configured to engage a distal end of the expandable anchor, and a distal end of the outer tube can be configured to engage a proximal end of the expandable anchor.

In another embodiment, the expandable anchor can be configured to expand upon movement of a distal end of the expandable anchor toward a proximal end of the expandable anchor. For example, the obturator can be configured to engage the proximal and distal ends of the expandable anchor and can move the proximal and distal ends of the expandable anchor toward one another to expand the expandable anchor.

In another exemplary embodiment, the obturator can include a keying element formed on a distal end thereof. The keying element can be configured to mate with a complementary keying element formed on a distal end the cannula such that rotation of the obturator can cause the corresponding rotation of the cannula.

In other aspects, a surgical access device is provided having a housing and a cannula extending distally from the housing. The cannula and the housing can define a working channel extending therethrough. The cannula can have an expandable anchor formed on a distal end thereof and it can be movable between an insertion configuration and an expanded deployed configuration. An obturator insertable through the working channel can be configured to move the expandable anchor between the insertion and deployed configurations. The obturator can be configured to selectively mate with the cannula such that rotation of the obturator can be effective to cause corresponding rotation of the cannula.

In one embodiment, the access device can include a rotatable member coupled to the obturator such that rotation of the rotatable member can be effective to cause the obturator to move the expandable anchor between the insertion and deployed configurations.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
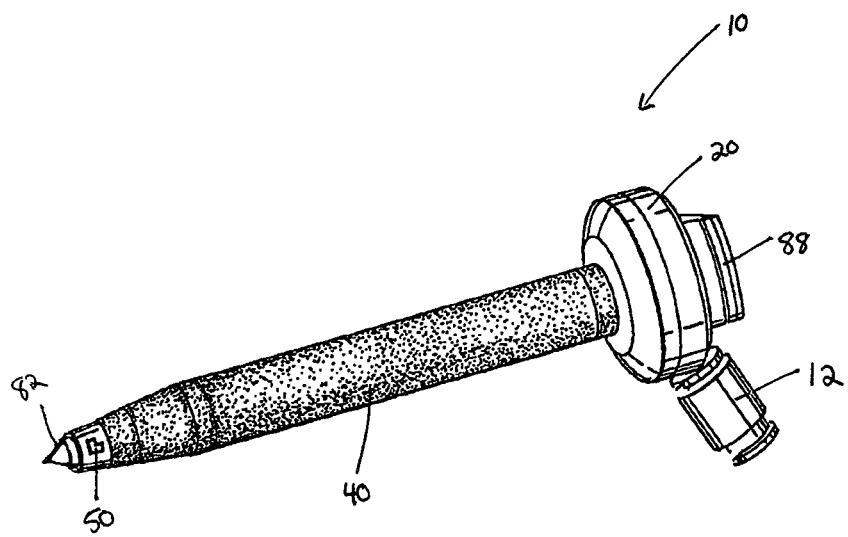
FIG. 1 is a perspective view of one embodiment of a surgical access device having a housing, a cannula, and an obturator, with the cannula shown in an insertion configuration.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for surgically accessing a body cavity. In general, the methods and devices allow a surgical access device to be securely positioned within an opening in tissue to provide access to a body cavity underlying the tissue. The various surgical access devices can include a housing configured to be at least partially disposed outside a patient's body and an elongate tubular member such as a cannula, wound protector, retractor, or other member for forming a pathway through tissue (hereinafter generally referred to as a cannula). The cannula can extend distally from the housing and it can be configured to be positioned within an opening in a patient's body, such as through skin. One or more surgical instruments can be inserted through the housing and the cannula to access a surgical site within the body.

In an exemplary embodiment, the access devices described herein can be configured to move between an insertion configuration and a deployed configuration following penetration of the body wall to help securely position the device within the tissue and/or to provide active retraction of the opening formed in the tissue. All or a portion of the cannula can radially expand when the access device is moved from the insertion configuration to the deployed configuration. Such secure positioning can help form a better seal between the tissue and the device and it can help retain the device in a more stable position relative to the tissue. The device can also optionally dilate the tissue when positioned therein to help improve the seal integrity between the device and the tissue. Such dilation of the tissue by the device can increase a size and/or change the shape of the opening in the tissue to increase working space available through the tissue opening. Having more working space through the tissue can help reduce interference between multiple surgical instruments inserted therethrough and/or allow larger and/or a greater number of surgical instruments to be inserted therethrough. The configuration of the surgical access devices can allow for use with a variety of tissue thicknesses and can reduce the extension of the surgical access devices into the body cavity where the surgical access devices could harm structures within the body cavity and/or interfere with instruments performing a surgical procedure.

Figure 2:
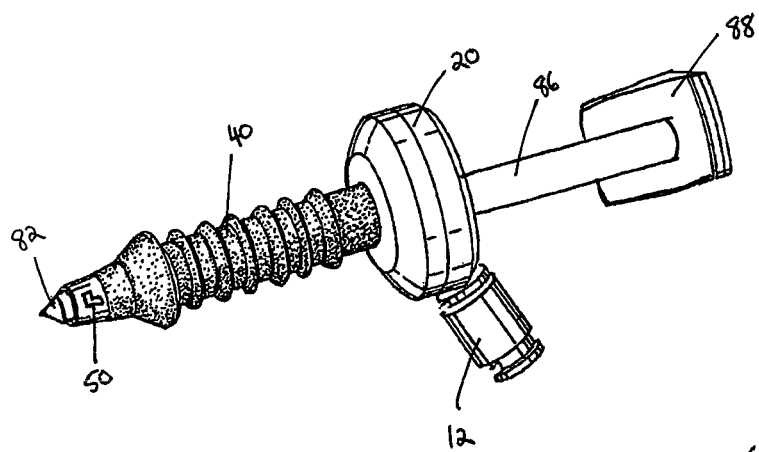
FIG. 2 is a perspective view of the access device of FIG. 1 with the cannula in the deployed configuration.

FIGS. 1-5 illustrate one exemplary embodiment of an access device. The access device 10 generally includes a housing 20 having a cannula 40 extending distally therefrom, and an obturator 80 disposable through the housing 20 and cannula 40. The housing 20 and the cannula 40 can define a working channel extending through the access device 10 for slidably and removably receiving the obturator 80 and/or any number of other surgical instruments therein. When the obturator 80 is disposed therein, a distal tip 82 of the obturator 80 can extend through and beyond a distal end of the cannula 40 to penetrate the body wall and to aid in inserting the cannula 40 through tissue. The cannula 40 can be configured to transition from an insertion configuration, as shown in FIG. 1, to a deployed configuration, as shown in FIG. 2, to securely position the access device within the tissue. While any portion of the cannula 40 can change when the cannula 40 is moved between the insertion and deployed configurations, in an exemplary embodiment the cannula 40 includes a distal anchoring element 46 that expands radially outward when the cannula is moved from the insertion configuration to the deployed configuration. The access device 10 can also include an engagement feature for locking the obturator 80 and the cannula 40 in a fixed position relative to one another. The access device 10 can also include any number of other features including, by way of non-limiting example, an insufflation port 12, one or more seal elements 14, and an actuation mechanism as will be discussed below.

The housing 20 can have a variety of sizes, shapes, and configurations. Generally, the housing can be configured to be positioned external to the patient's body cavity and it can be configured to provide a pathway for receiving a surgical instrument. A distal surface of the housing can be configured to rest on or engage the exterior surface of a body wall to prevent the access device from being pushed into the body cavity. Although not shown, one skilled in the art will appreciate that the housing can include any number of features to facilitate securely engaging the housing to the exterior surface of the body wall such as, by way of non-limiting example, surface features formed on the distal surface of the housing or suture anchors coupled to the housing to aid in securing the housing to the body wall. The housing can include zero, one, or multiple seal elements to receive one or more instruments extending through the working channel. Exemplary housing configurations are described in more detail in U.S. Pat. No. 6,017,356 entitled "Method For Using A Trocar For Penetration And Skin Incision", issued on Jan. 25, 2000, U.S. Patent Publication No. 2004/0230161 entitled "Trocar Seal Assembly," filed on Mar. 31, 2004, and in U.S. Patent Publication No. 2007/0185453 entitled "Conical Trocar Seal," filed on Oct. 15, 2003, which are hereby incorporated by reference in their entireties.

Figure 4:
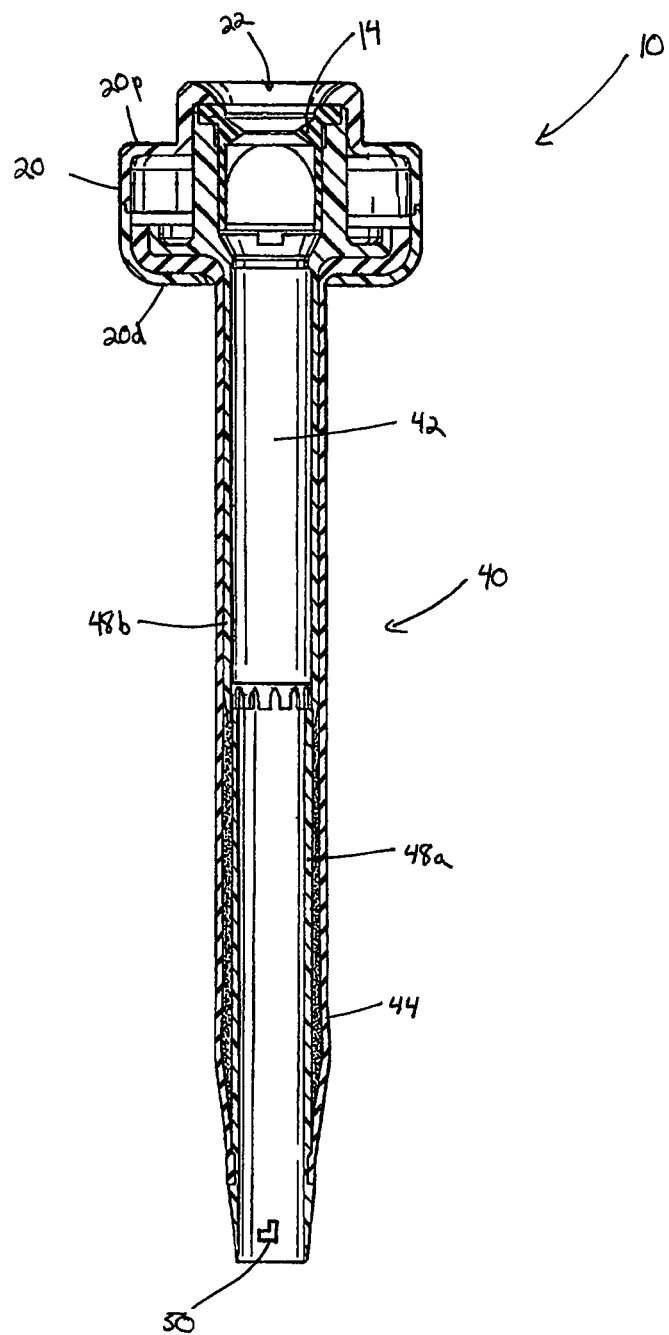
FIG. 4 is a cross-sectional view of the access device of FIG. 1 with the cannula in the insertion configuration.
Figure 5:
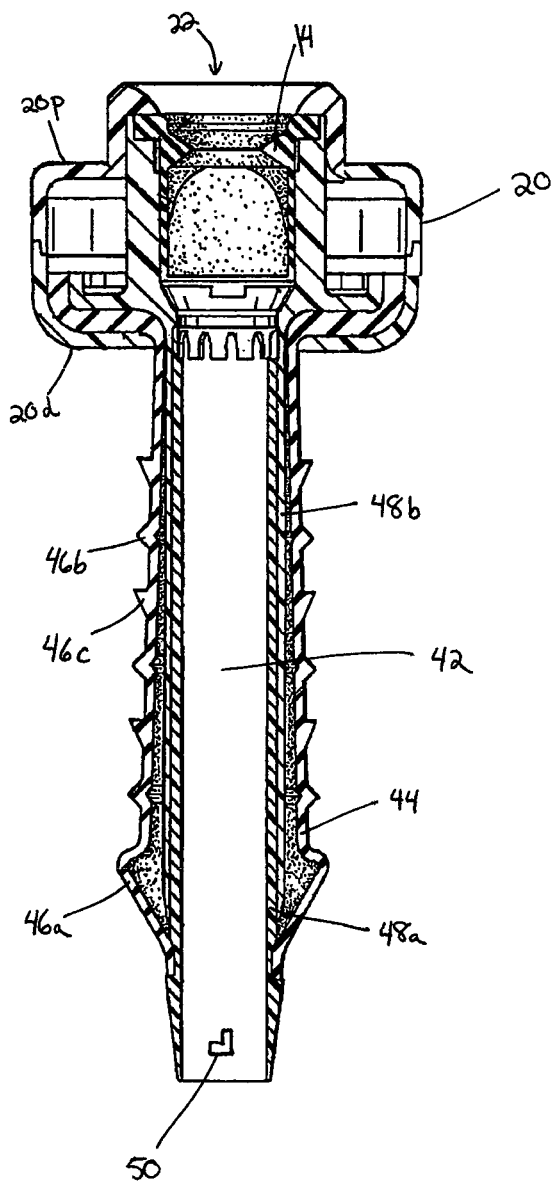
FIG. 5 is a cross-sectional view of the access device of FIG. 1 with the cannula in the deployed configuration.

As shown in more detail in FIGS. 4 and 5, in the illustrated embodiment the housing 20 is generally in the form of an annular disc having a central opening 22, a proximal surface 20p, and a distal surface 20d. As will be discussed in detail below, the proximal surface 20p can be configured to engage an obturator. Although not shown in FIGS. 4 and 5, the proximal surface 20p of the housing 20 can include any coupling mechanism known in the art (e.g., snap rings, bores, etc.) to allow the housing 20 to removably couple to an obturator. One or more seal elements 14 can be disposed across the working channel of the housing 20.

The cannula can have a variety of sizes, shapes, and configurations. Generally, the cannula extends distally from the housing and is positionable within an opening in a patient's body, whether through a natural opening or a surgical incision. By way of non-limiting example, the cannula can be inserted through the umbilicus. The cannula can be integral with or fixedly or removably coupled to the housing in any manner known in the art (e.g., welded, snap-fit, threads, ball and socket elements, male-female couplings, etc.). Generally a distal portion of the cannula can extend into a body cavity, for example within the abdominal cavity, while a proximal portion of the cannula is positioned within the tissue opening. A lumen in the cannula can define a working channel and form a pathway through the opening so that surgical instruments can be inserted from outside the body through the housing and cannula and into an interior body cavity. In one embodiment, the cannula can be substantially flexible so that it can be easily maneuvered into and within tissue as needed. In other embodiments, the cannula can be substantially rigid or substantially semi-rigid. The cannula can be formed of any suitable material known in the art, e.g., silicone, urethane, thermoplastic elastomer, and rubber. One of skill in the art will appreciate that the cannula can include any number of additional features to facilitate providing access through a body wall. Although the cannula need not include any seal elements, one or more seal elements can be disposed across the working channel of the cannula to seal one or more instruments extending therethrough.

In an exemplary embodiment, the cannula is movable between an insertion configuration for insertion through tissue, and a deployed configuration for anchoring within the tissue. In general, the cannula can have an elongated configuration in the insertion position in which a maximum outer diameter of the cannula is reduced to ease insertion through a body wall, and it can have a radially expanded and/or axially contracted configuration in the deployed position to aid in the retention of the access device within the tissue opening and/or to reduce the length of the cannula extending into the body cavity. In some embodiments, for example, the cannula has a length in the insertion configuration that is greater than the length of the cannula in the deployed configuration, and/or the cannula has a maximum outer diameter in the insertion configuration that is less than the maximum outer diameter of the cannula in the deployed configuration. The cannula can also be configured to have a biased configuration. By way of non-limiting example, the cannula can be biased to the insertion configuration such that a proximally-directed force is required to transition the cannula to the deployed configuration. In an exemplary embodiment, the cannula is biased to the deployed configuration such that a distally-directed force is required to maintain the cannula in the insertion configuration.

In some embodiments, the distal portion of the cannula can act as an anchor to engage the interior surface of the tissue wall. The anchor can help securely retain the access device within the tissue opening and prevent the access device from being accidentally removed during surgery. The distal portion of the cannula can have a variety of sizes, shapes, and configurations but generally has a maximum outer diameter that is greater than a maximum outer diameter of the proximal portion of the cannula when the cannula is in the deployed configuration. Exemplary embodiments of cannula anchors are described in more detail in U.S. patent application Ser. No. 12/636,174 entitled "Methods and Devices for Providing Access Through Tissue to a Surgical Site," filed Dec. 11, 2009, and in U.S. patent application Ser. No. 12/636,205 entitled "Methods And Devices For Providing Access Through Tissue To A Surgical Site," filed Dec. 11, 2009, which are hereby incorporated by reference in their entireties.

An exemplary embodiment of a cannula is shown in more detail in FIGS. 4 and 5. The cannula 40 extends distally from the housing 20 and defines a working channel 42 for passage of a surgical instrument. The cannula 40 can include a telescoping inner tube 48a, an outer tube 48b that slidably receives the inner tube 48a, and an elastically-deformable outer sleeve 44. The telescoping inner tube 48a can be axially movable relative to the outer tube 48b. The proximal end of the outer tube 48b can extend from or be coupled to the housing 20 and the distal end of the inner tube 48a can extend from or be coupled to the distal end of the outer sleeve 44. The inner tube 48a can be freely slidable relative to the outer tube 48b. One skilled in the art will appreciate that the inner tube 48a can alternatively be coupled to or extend from the housing, and the outer tube 48b can be coupled to the distal end of the sleeve 44, and be freely slidable relative to the inner tube 48a.

The outer sleeve 44 can have a substantially cylindrical shape in the insertion configuration, as shown in FIGS. 1 and 4, and a radially-expanded, outwardly tapering shape in the deployed configuration, as shown in FIGS. 2 and 5. When in the deployed configuration, the distal portion of the outer sleeve 44 can radially expand to form an anchor 46a for securing the access device 10 against the interior surface of the body wall. The surface of the outer sleeve 44 can also include a plurality of additional surface features 46b, 46c to aid in the retention of the cannula 40 within the tissue opening and to prevent movement of the cannula 40 in the proximal direction when the cannula 40 is in the deployed configuration.

The sleeve 44 can be configured to be biased as shown in FIG. 5, such that the sleeve 44 in a resting configuration has a longitudinally contracted and radially expanded configuration, with the inner tube 48a withdrawn into the outer tube 48b. The cannula 40 can be transitioned to the insertion configuration, as shown in FIG. 4, with a distally-directed force on the distal end of cannula 40, thereby longitudinally extending the deformable sleeve 44 and sliding the inner tube 48a distally relative to the outer tube 48b. The sleeve 44 can be formed from a variety of materials known in the art, including for example various plastics, silicone, polyisoprene, other elastomers or rubbers, and/or any combination thereof. The material or materials chosen for the sleeve 44 can have a combination of optimal attributes such as flexibility, strength, durability, breathability, microbial resistance, etc. By way of non-limiting example, the sleeve 44 can be formed as a mesh or an impermeable sheath.

Another embodiment of an exemplary cannula and housing are described in U.S. Patent Publication No. 2008/0086080 entitled "Elastically Deformable Surgical Access Device Having Telescoping Guide Tube," filed on Apr. 13, 2007, which is hereby incorporated by reference in its entirety.

The obturator can also have a variety of shapes, sizes, and configurations. Generally, the obturator can include an elongate shaft having a proximal handle configured to be disposed outside a patient's body and a distal end with a tip configured to be inserted through tissue. The obturator can be a solid member or it can be substantially hollow. The shaft of the obturator can be substantially flexible or rigid. By way of non-limiting example, the shaft can be formed from a flexible material, and/or it can include one or more features formed therein to facilitate flexibility, such as a plurality of cut-outs or slots. The shaft can also include regions that vary in flexibility. Varying flexibility of the shaft can be achieved in a variety of ways as will be appreciated by a person skilled in the art, such as by forming the shaft from different materials, varying the diameter or thickness of the shaft, etc. The shaft can also include other features to facilitate use, such as one or more spiral wires embedded therein and configured to preventing kinking of the shaft.

Figure 3:
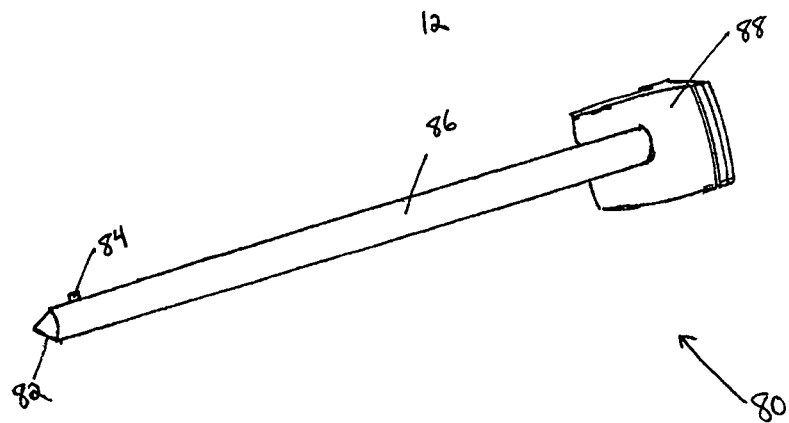
FIG. 3 is a perspective view of the obturator of FIG. 1.

The size and shape of the obturator can vary, but as shown in one exemplary embodiment depicted in FIGS. 1-3, the shaft 86 of the obturator 80 can have a longitudinal length greater than a longitudinal length of the access device 10 in the insertion configuration such that the obturator 80 can be inserted through the working channel with the handle 88 located just proximal to the housing 20 and the distal tip 82 located distal to the distal end of the cannula 40. The handle 88 can have a maximum diameter greater than a diameter of at least a proximal-most opening in the working channel of the housing 20, thereby preventing the handle 88 from passing through the housing 20. The obturator 80 can be configured to rotate about its longitudinal access, but it can also be selectively fixed relative to the housing 20 and cannula 40 such that rotation of the obturator 80 causes corresponding rotation of the housing 20 and cannula 40.

The distal tip 82 of the obturator 80 can have a variety of shapes, sizes, and configurations. Generally, the tip 82 can be configured to penetrate tissue. The tip 82 can be formed from one or more flexible and/or rigid materials, such as stainless steel, titanium, etc., to help the tip 82 penetrate tissue. In an exemplary embodiment, the obturator 80 can be hollow and the tip 82 can be transparent to allow visualization therethrough. By way of non-limiting example, an endoscope (not shown) can be proximally inserted into the obturator 80 to provide visualization through a transparent distal tip 82. The tip 82 can have a variety of shapes and sizes, e.g., conical (as shown in FIG. 1), triangular, rectangular, rounded, etc. The tip 82 can be integrally formed with the shaft 86, or can be removably or fixedly attached to the shaft 86, e.g., through an interference fit, an adhesive, ultrasonic welding, etc. The tip 82 can also be set substantially off-center of the longitudinal axis of the shaft 86 such that the tip 82 is self-tapping to ease insertion and minimize damage to the tissue. One of skill in the art will appreciate that the tip 82 can include one or more features to help penetrate tissue, e.g., tissue-separators, a tapered shape, a beveled edge (including a chamfered edge), a pointed needle, an electronic cutter, a sharp cutting blade, etc. By way of non-limiting example, the tip 82 can include one or more tissue-separating wings that extend radially outward from the tip 82 to assist in moving the tip 82 through tissue and to help minimize damage to the tissue. Exemplary configurations for the tip 82 are described in U.S. Patent Application No. 2007/0260121 entitled "Endoscopic Translumenal Surgical Systems," filed May 8, 2006, U.S. patent application Ser. No. 12/478,882 entitled "Multiplanar Obturator with Foldable Retractor," filed Jun. 5, 2009, and U.S. Patent Application No. 2007/0260273 entitled "Endoscopic Translumenal Surgical Systems," filed May 8, 2006, which are hereby incorporated by reference in their entireties.

In an exemplary embodiment, the distal end of the cannula can include one or more engagement features formed thereon or coupled thereto for releasably mating with one or more complementary engagement features formed on an obturator. As shown in FIGS. 1-5, the distal end of the obturator 80 can be configured to engage the distal end of the cannula 40. While virtually any engagement technique can be used, including bayonet-type engagement mechanisms, in the illustrated embodiment the obturator 80 includes a protrusion 84 extending radially outward from an outer perimeter of the obturator 80, e.g., from an outer sidewall of the obturator 80, and at least one corresponding opening 50 is formed in the distal end of the cannula 40. The opening 50 can include a longitudinally-extending portion in which the protrusion 84 can be inserted into and/or removed from the opening 50 in a proximal-distal direction, and a radially-extending portion in which the protrusion 84 can laterally slide to lock and unlock the protrusion in the opening. The protrusion 84 and opening 50 can have any shape and size that allow the protrusion 84 to be inserted into the longitudinal portion of the opening 50 and to slide within the circumferential portion of the opening 50. The obturator 80, with the cannula 40 keyed thereto through engagement of the protrusion 84 and the opening 50, can be rotated in a first direction, e.g., a clockwise direction, relative to the cannula 40, thereby causing the protrusion 84 to travel laterally within the opening 50 to a position in which the protrusion 84 abuts the terminal end of the circumferential portion of the opening 50, thereby locking the distal end of the obturator 80 to the cannula 40. The opening 50 can angle proximally or distally (not shown) at its terminal end such that the protrusion 84 can proximally or distally slide and snap into the terminal end to help ensure that the protrusion 84 is fully engaged with the opening 50. In the illustrated embodiment, the protrusion 84 can move in only one direction (e.g., clockwise) to lock the obturator 80 to the cannula 40 because the circumferential portion of the opening 50 extends in a single direction from the longitudinal portion of the opening 50. Similarly, in the illustrated embodiment, the longitudinal portion of the opening 50 extends proximally from the circumferential portion such that the protrusion 84 can be removed proximally from the opening 50 formed in the distal end of the cannula 40 when the protrusion 84 is longitudinally aligned with the longitudinal portion of the opening 50. One skilled in the art will appreciate, however, that the circumferential portion of the opening 50 can extend in both directions from the longitudinal portion of the opening 50 such that rotation of the obturator 80 in either direction (i.e., clockwise or counter-clockwise) can be effective to lock the obturator 80 relative to the distal end of the cannula 40.

In use, the surgical access device 10 can provide access to a patient's body cavity. The cannula 40 is positionable within an opening in a patient's body such that a distal portion of the cannula 40 extends into a patient's body cavity and a proximal portion of the cannula is positioned within the tissue opening. A lumen in the cannula 40 can define a working channel and form a pathway through the opening in a patient's body so that surgical instruments can be inserted from outside the body to an interior body cavity.

Prior to insertion of the access device 10 through a patient's body wall, and with the cannula 40 biased in the deployed configuration, as shown in FIG. 2, the obturator 80 can be inserted into the working channel of the housing 20 and cannula 40 such that the distal end of the obturator 80 engages the distal end of the cannula 40. The distal end of the obturator can be keyed to the distal end of the cannula 40 through the coupling of the complementary engagement features of the distal ends of the obturator 80 and cannula 40. For example, the protrusion 84 may be aligned with and inserted into the longitudinal portion of the opening 50, and the obturator 80 can be rotated relative to the cannula 40 such that the protrusion 84 slides along the circumferential portion of the opening 50 to fully engage the complementary engagement mechanisms. Subsequent distal extension of the obturator 80 relative to the housing 20 can be effective to transition the cannula 40 from the deployed configuration to the insertion configuration. While not shown, the obturator housing can include a latch or other feature that engages a corresponding feature formed on the housing of the cannula to thereby lock the obturator within the cannula when the obturator is fully deployed into the cannula and the cannula is in the insertion configuration.

The cannula 40 can be inserted through a natural opening, a surgical incision, or can be configured to penetrate the body wall. For example, the surgeon can pierce the body wall with the obturator tip 82 and provide a distally-directed force to force the cannula 40 through the body wall. Additionally, rotation of the obturator 80 can be effective to aid in penetrating the cannula 40 through the body wall and into the body cavity. Although the compressive forces of the tissue opening would tend to engage the cannula 40 thus causing the obturator 80 to rotate within the cannula, the keying of the distal end of the cannula 40 to the obturator 80 can lock the two components together causing the cannula 40 and obturator 80 to rotate as a unit. That is, the obturator 80 and the cannula 40 are fixed relative to one another when the complementary engagement features are mated such that rotation of the obturator 80 can be effective to cause corresponding rotation of the cannula 40.

When the housing 20 is seated on the exterior surface of the body wall, the cannula 40 can be transitioned from the insertion configuration to the deployed configuration. For example, when the obturator 80 is keyed to the cannula 40, the obturator 80 can be pulled distally relative to the cannula 40 to cause or allow the expandable sleeve 44 to revert to its biased configuration, thereby withdrawing the inner tube 48*a* within the outer tube 48*b* and expanding the distal anchoring element 46. In particular, as the obturator 80 is pulled proximally, the distal end of the cannula 40 is pulled toward the proximal end of the cannula 40, causing the expandable sleeve 44 to decrease in length and causing the distal anchoring element 46 to expand radially outward and engage the interior surface of the body wall to lock the access device within the tissue wall. Expansion can occur as a result of the folding or accordion-type configuration of the sidewalls of the sleeve 44. The obturator 80 can then be rotated to un-key the obturator from the cannula 40. For example, the obturator 80 can be rotated to align the protrusion 84 with the longitudinal portion of the opening 50 such that the obturator 80 can be pulled proximally to disengage the protrusion 84 from the opening 50 and to remove the obturator 80 from the access device 10. Various tools/instruments can then be inserted through the cannula 40. Once the procedure is complete, the obturator 80 can be reinserted into the cannula 40, rotated to cause the engagement mechanisms to mate, and then moved further distally within the cannula to cause the cannula to move to the insertion configuration. The access device 10 can then be removed from the tissue wall.

Figure 6:
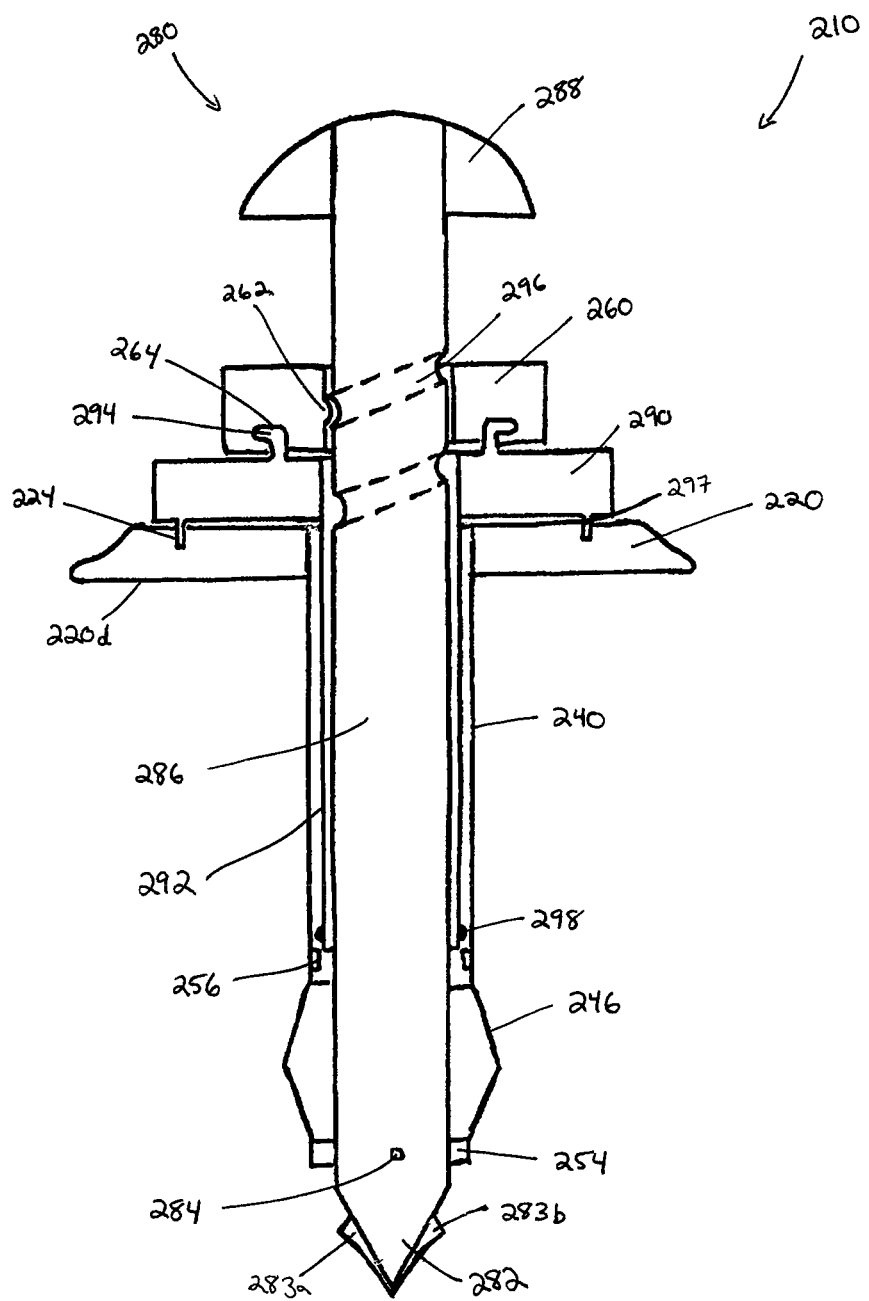
FIG. 6 is a partial cross-sectional view of another embodiment of a surgical access device.
Figure 7A:
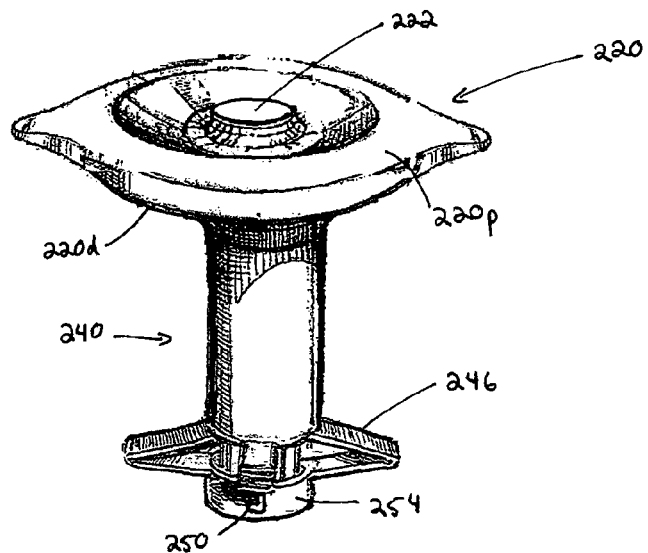
FIG. 7A is a perspective view of cannula of the access device of FIG. 6 in a deployed configuration.
Figure 7B:
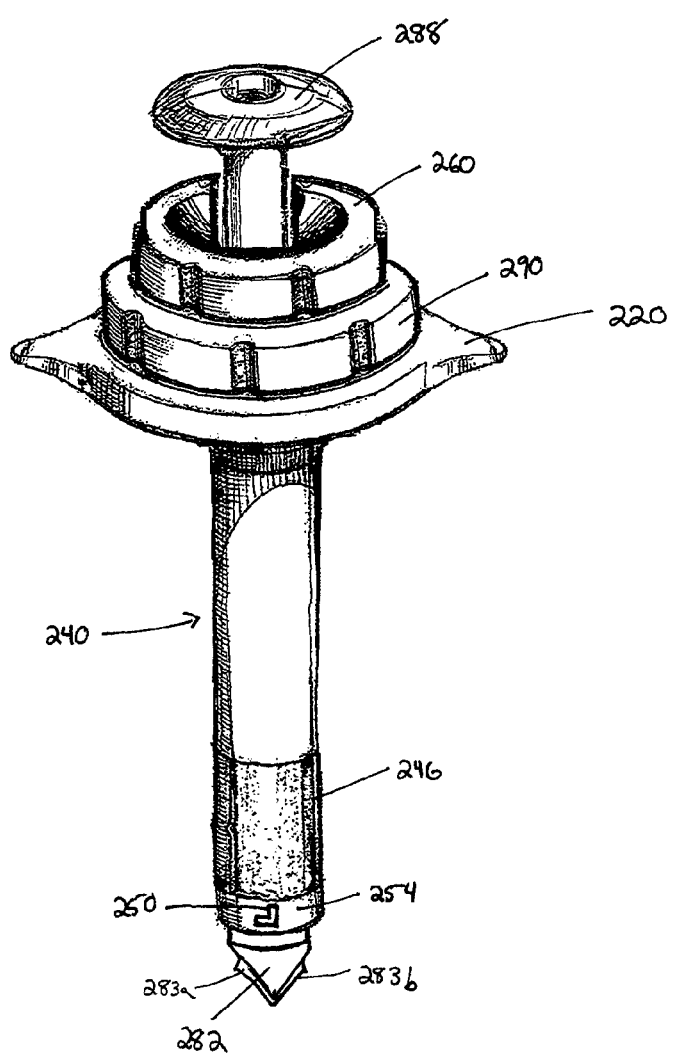
FIG. 7B is a perspective view of the access device of FIG. 6 with the cannula in an insertion configuration.
Figure 7C:
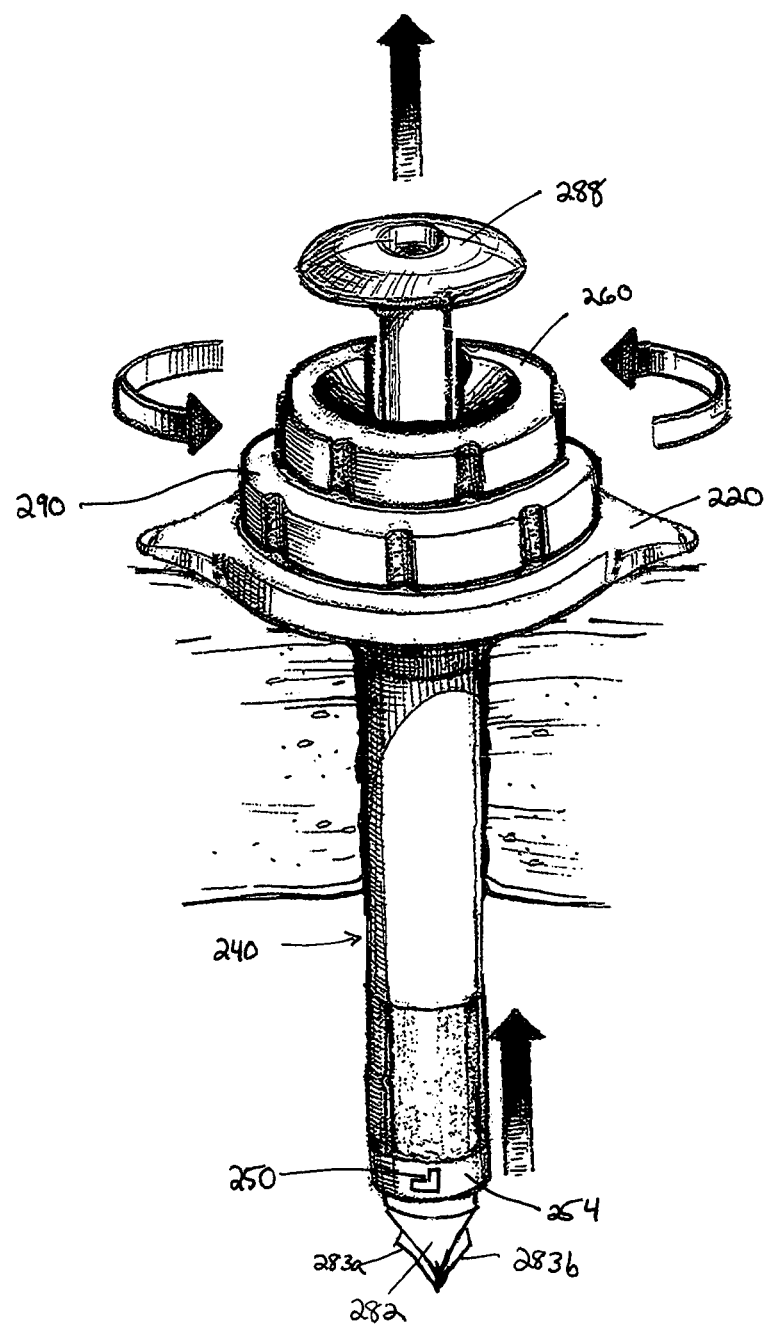
FIG. 7C is a perspective view of the access device of FIG. 6 extending through a body wall with the cannula in an insertion configuration.
Figure 7D:
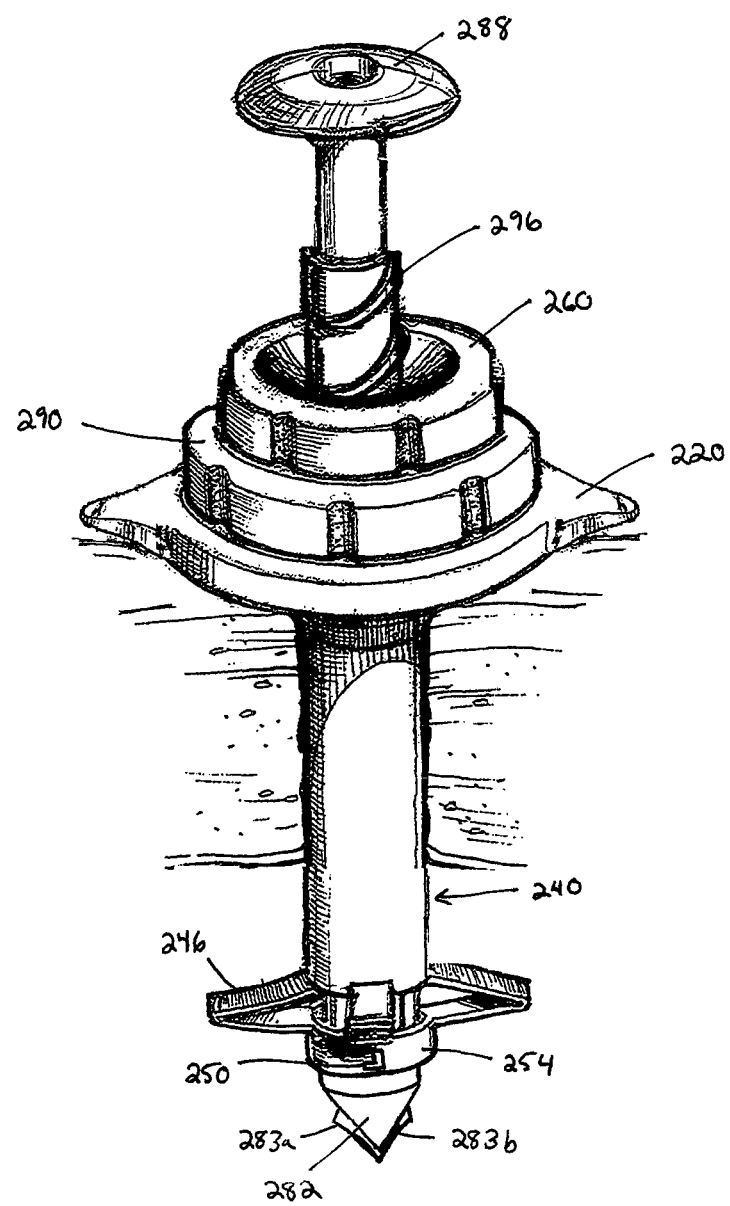
FIG. 7D is a perspective view of the access device of FIG. 7C with the cannula moved to a deployed configuration.
Figure 7E:
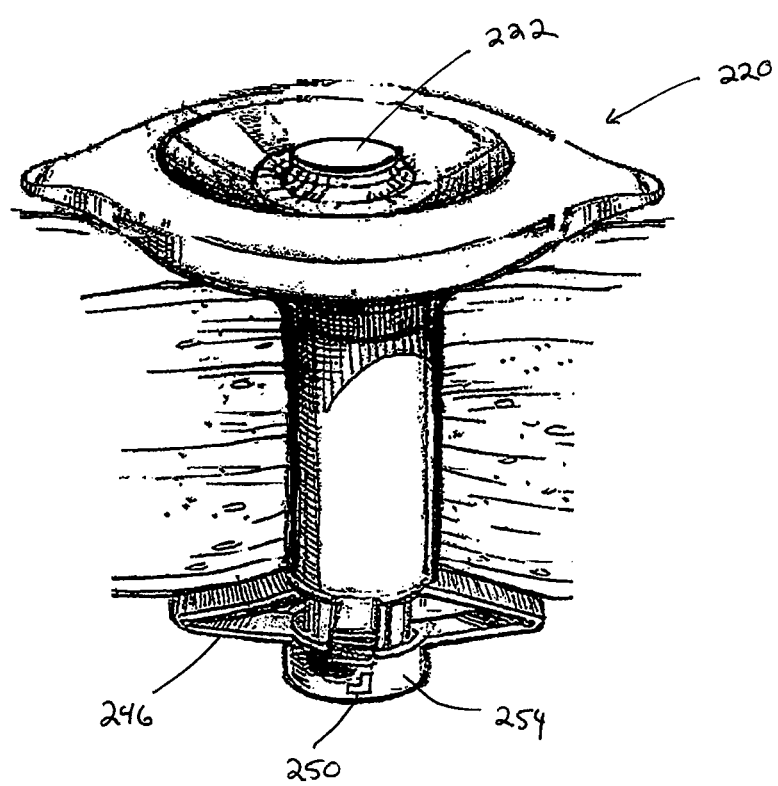
FIG. 7E is a perspective view of the cannula of the access device of FIG. 7D engaged with the body wall in a deployed configuration.

In another embodiment, shown in FIGS. 6-7E, the obturator 80 can be operatively associated with an actuation mechanism that is effective to transition the cannula 40 between the insertion configuration to the deployed configuration. The access device 210 is similar to access device 10 and generally includes a housing 220 and a cannula 240 extending distally from the housing 220. The housing 220 and the cannula 240 can define a working channel extending through the access device 210. The distal portion of the cannula 240 can include an expandable anchor 246 that is configured to transition from an insertion configuration, as shown in FIG. 7B, to a deployed configuration as shown in FIG. 7A. The access device 210 can also include an obturator 280. In this embodiment, the obturator 280 has an inner tube 286 and an outer tube 292 with a proximal head 290 formed thereon. The obturator 280 also includes a rotatable actuation mechanism 260 operatively associated with the inner and outer tubes 286, 292 and effective to move the inner tube 286 relative to the outer tube 292 to cause the expandable anchor 246 to expand.

As discussed above, the housing 220 can be configured to be positioned external to the patient's body cavity and can have a variety of shapes, sizes, and configurations. As shown, the housing 220 is generally in the form of an annular disc having a central opening 222, a proximal surface 220*p*, and a distal surface 220*d*. The distal surface 220*d* of the housing 220 can be configured to rest on or engage the exterior surface of a body wall when the access device 210 is positioned within a tissue opening. The proximal surface 220*p* can be configured to engage an obturator 280 and can include any variety of coupling mechanisms known in the art to allow the housing 220 to removably couple to the obturator 280. As shown in FIG. 6, for example, the proximal surface 220*p* can include a plurality of bores 224 for receiving latches or pins 297 extending distally from the head 290 of the obturator 280.

The cannula 240 extends distally from the housing 220 and can provide a working channel through a tissue opening. The distal portion of the cannula 240 includes an expandable anchor 246 and an annular member 254 having a keying element for coupling to a complementary keying element of the obturator 280. The anchor 246 can generally be configured to transition from an insertion configuration in which the anchor 246 has a first outer diameter to a deployed configuration in which the anchor 246 has a second outer diameter that is greater than the first outer diameter. In the insertion configuration, the expandable anchor 246 preferably has a diameter that is the same as the diameter of the proximal portion of the cannula 240, and in the deployed configuration, the expandable anchor 246 can have a diameter greater than the diameter of the proximal portion of the cannula 240. The anchor 246 can have virtually any configuration. By way of non-limiting example, the anchor 246 can be in the form of, for example, a plurality of flexible cables, strings, threads, bands, ribbons, strips, or wires, generally referred to as "wires", spaced apart from one another and configured to longitudinally collapse and radially expand when the anchor 246 moves from the insertion configuration to the deployed configuration. Although not shown, a protective sleeve can be disposed around the anchor 246 to protect the wires and prevent the wires from snagging on tissue or other matter. Further, the protective sleeve can optionally include gripping features (not shown), e.g., a textured surface, a non-slip coating, etc., configured to help grip tissue and reduce slippage of the anchor 246 when the anchor 246 is deployed and abuts the interior surface of the body wall. Additionally, the cannula 240 can include an annular shoulder 256 formed on an inner surface thereof for engaging the distal end of the outer tube 292 of the obturator 280. The annular shoulder 256 can be located, for example, just proximal to the anchor 246.

As shown in FIG. 6, the obturator 280, which can be disposed in the working channel defined by the housing 220 and the cannula 240, generally includes an outer tube 292 and inner tube 286. The inner tube 286 is generally an elongate member and can include a proximal handle 288 and a distal tip 282. As discussed above, a keying element can be formed on the distal portion of the inner tube 286 for engagement with a corresponding keying element on the distal end of the cannula 240, and in particular on the distal end of the anchor 246 of the cannula 240. For example, a protrusion 284 can extend radially outward from the distal portion of the inner tube 286 for keying with an opening 250 formed in the annular member 254. The tip 282 can also include various features as previously described with respect to tip 82. For example, tip 282 can include one or more tissue-separating wings 283a, 283b that extend radially outward from the tip 282 to assist in moving the tip 282 through tissue and to help minimize damage to the tissue. The tip 282 can also in other embodiments be transparent to allow viewing through the tip 282, e.g., with an endoscope. The inner tube 286 can have a sufficient longitudinal length such that, when the cannula 240 is in the insertion configuration, the inner tube 286 can be disposed through the lumen of the outer tube 292 and through the working channel of the housing 220 and cannula 240 with the handle 288 located proximal to the housing 220 and the distal tip 282 located distal to the distal end of the cannula 240.

At least a portion of the inner tube 286 can include a groove or guide channel 296 formed on an outer surface thereof for threadingly receiving a detent 262 of the rotatable knob 260, as will be discussed in more detail below. In an exemplary embodiment, the guide channel 296 extends radially around an outer surface of the inner tube 286 at an angle relative to a longitudinal axis of the inner tube 286. The guide channel 296 can have any length, for example, it can extend 30 degrees, 60 degrees, 90 degrees, etc. around the inner tube 286. The length of the guide channel 296 preferably corresponds to the distance that the outer tube 292 needs to move relative to the inner tube 286 to cause expansion of the distal anchor. The terminal ends of the guide channel 296 can include a stop feature for preventing further rotational movement of the detent 262 along the guide channel 296 and for frictionally engaging the detent 262 to maintain the detent 262 therein by interference fit, thereby maintaining the inner and outer tubes in a fixed axial position relative to one another. For example, a dimple (not shown) formed in the proximal terminal end of the guide channel 296 can engage the detent 262 such that further motion of the inner tube 286 relative to the outer tube 292 can be restricted. Similarly, a dimple (not shown) formed in the distal terminal end of the guide channel 296 can engage the detent 262 such that further motion of the inner tube 286 relative to the outer tube 292 can be restricted. One skilled in the art will appreciate that the inner tube 286 can alternatively include a detent or raised threads and the rotatable knob 260 could include a corresponding guide channel or complementary threads for axially translating the inner member 286 with rotation of the rotatable knob 260.

The outer tube 292 is configured to be disposed within the working channel defined by the housing 220 and the cannula 240, and it can be a generally cylindrical member having a lumen formed therein. The distal end of the outer tube 292 can include an engagement feature for engaging the annular shoulder 256 of the cannula 240. For example, a grommet 298 can be disposed around an outer surface of the distal portion of the outer tube 292 for forming an interference or friction fit with the annular shoulder 256. The outer tube 292 can also include a proximal head 290 that is configured to engage a proximal surface 220p of the housing 220. As shown in FIG. 6, the head 290 includes a snap ring 294 extending proximally from its proximal surface 290p that is configured to be received within an annular recess 264 formed within a distal surface of the rotatable knob 260 such that the rotatable knob 262 can be freely rotated relative to the outer tube 292. A person skilled in the art will appreciate that various techniques can be used to freely, rotatably mate the rotatable knob 262 to the head 290 of the outer tube 292. The distal surface 290d of the head can include an engagement mechanism for removably coupling the obturator 280 to the housing 220. For example, pins 297 can extend distally from the distal surface 290d of the head to removably engage bores 224 formed in the proximal surface 220p of the housing 220 by compression fit, snap-fit, etc.

The actuation mechanism can also have a variety of shapes, sizes, and configurations. Generally, the actuation mechanism is operatively associated with the obturator and can be effective to move the cannula from the insertion configuration to the deployed configuration when the obturator is disposed within the cannula.

As shown in FIGS. 6-7E, the actuation mechanism can be a rotatable knob 260 freely rotatably coupled to the proximal surface of the head 290 of the outer tube 292 and in engagement with the inner tube 286. The rotatable knob 260 can be generally shaped as an annular disc having a proximal surface, a distal surface, and an inner wall defining a central opening through which the inner tube 286 can be disposed. The distal surface of the rotatable knob 260 can include an annular recess 264 configured to receive the snap ring 294 formed on the proximal surface of the head 290 of the outer tube 292, as discussed above, such that the rotatable knob 260 is freely rotatable relative to the head 290 and outer tube 292. The rotatable knob 260 also includes a detent 262 that extends radially inward from the inner wall of the rotatable knob 260. The detent 262 can be configured to extend into and engage the guide channel 296 formed in the inner tube 286 of the obturator such that rotation of the knob 260 is effective to axially translate the inner member 286 in a proximal/distal direction relative to the outer member 290 as the detent 262 moves through the guide channel 296. A person having ordinary skill in the art will appreciate that the rotatable knob 260 can include additional features (e.g., rotation locks) to selectively restrict the rotatable knob 260 from rotating relative to the obturator 280.

In use, the surgical access device 210 can be effective to provide access to a patient's body cavity. FIG. 7A illustrates the access device 210 with the anchor 246 biased in the deployed configuration, prior to the inserting the obturator 280 through the cannula. When the obturator 280 is inserted into the cannula 240, as shown in FIG. 7B, the inner tube 286 and outer tube 292 will extend through the working channel. The head 290 on the outer tube 292 can be advanced into engagement with the housing 220, e.g., through engagement of the pins 297 with the bores 224. As the head is advanced 290 is advanced toward the housing 220, the grommet 298 at the distal end of the outer tube 292 will engage the annular shoulder 256 of the cannula 240 to stretch the cannula distally, thereby moving the cannula into the insertion configuration, as shown in FIG. 7B. The inner tube 286 can similarly move the distal anchor into the insertion configuration. The engagement feature 284 on the distal end of the inner tube 286 can engage the engagement feature 250 formed in the annular member 254. In this position, the distal tip 282 of the inner tube 292 will extend beyond the distal end of the cannula 240. The inner tube 286 can optionally be rotated to key the corresponding engagement features 250, 284. With the distal end of the inner tube 286 locked relative to the distal end of the cannula 240, rotation of the rotatable knob 260 can cause the inner tube 286 to move distally within and relative to the outer tube 292, thereby effectively increasing a length of the obturator 280 extending distally from the housing 220. Distal movement of the inner tube 286 will push the distal end of the cannula 240, and in particular the distal end of the anchor 246, distally relative to a proximal end of the anchor 246, thereby causing the expandable anchor 246 to stretch longitudinally, and decrease in diameter, e.g., to move to the insertion configuration shown in FIG. 7B.

The cannula 240, with the obturator 280 disposed therein, can be inserted through a natural opening, penetrated through tissue, or inserted through a surgical incision. For example, the surgeon can pierce the body wall with the distal tip 282 of the inner tube 286 and provide a distally-directed force to the access device 210 to force the cannula 240 through the body wall. In one embodiment, rotation of the head 290 on the outer tube 292 can also be effective to cause corresponding rotation of the cannula 240 to facilitate insertion through the body wall and into the body cavity. Although the compressive forces of the tissue opening would tend to grasp and prevent rotation of the cannula 240 relative to the obturator 280 during insertion, the keying of the distal end of the inner tube 286 of the obturator 280 to the cannula 240 can prevent independent rotation of the cannula 240.

When the housing 220 is seated on the exterior surface of the body wall, the anchor 240 can be transitioned from the insertion configuration to the deployed configuration. As shown in FIG. 9, rotation of the rotatable knob 260 about the proximal end of the outer tube 292 can be effective to axially move the inner tube 286 in a proximal direction relative to the outer tube 292. As a result, the distal end of the anchor 246 is moved proximally toward the proximal end of the anchor 246, thereby causing the anchor to collapse radially outward into its deployed configuration as shown in FIG. 7D. Prior to, during, and/or after the anchor 246 transitions from the insertion configuration to the deployed configuration, the distal end of the inner tube 286 can be disengaged from the distal end of the cannula 240. For example, the handle 288 can be rotated to disengage the engagement feature 284 on the inner tube 286 from the engagement feature 250 on the cannula 240. The engagement of the grommet 298 on the outer tube 292 with the annular shoulder 256 on the cannula 240 can be effective to retain the cannula 240 in an axially extended configuration. In other words, the obturator 280 can be used to deploy the anchor 246 while the obturator is still fully disposed within the cannula 240, and thus without the need to remove the obturator from the cannula. Such a configuration will ensure engagement of the inner wall of the tissue by the anchor before removal of the obturator. Once the anchor is deployed, the head 290 of the outer tube 292 can be pulled proximally to disengage the pins 297 from the bores 224. As the grommet 298 on the distal end of the outer tube 292 is moved proximally, the entire anchor 246 can move proximally toward the housing 220, resulting in axial compression or contraction of the cannula 240, as shown in FIG. 7E. The anchor 246 is thus pulled into further engagement with the interior surface of the body wall, thus capturing the tissue wall between the anchor 246 and the housing 220.

In any of the devices and methods discussed above, the cannula and/or anchor can return to its insertion configuration to ease removal of the access device following completion of the surgical procedure. For example, the access device can be prepared for removal by re-engaging the obturator with the distal end of the cannula (e.g., re-keying the complementary engagement features). The obturator can then be extended distally such that distal end of the cannula 40 extends distally and assumes its insertion configuration. The housing and obturator can then be pulled proximally to remove the access device 10 from the tissue opening. A person skilled in the art will appreciate that a separate removal device can also be provided to remove the access device.

The housing, cannula, actuation mechanism, and obturator can be formed from a variety of materials known in the art, including but not limited to various polymers, including polycarbonates and polyetheretherketone (PEEK), metals such as titanium or stainless steel, composites such as carbon-fiber reinforced PEEK, various ceramic materials, and/or any combination thereof. These structures can also be formed of various semi-rigid/flexible materials, including polyurethanes such as Pellethane (available from The Dow Chemical Company of Midland, Mich., USA), thermoplastic elastomers such as Santoprene (available from ExxonMobil Chemical of Houston, Tex., USA), polyisoprene elastomers, medium to high durometer silicone elastomers, and/or any combination thereof. A person having ordinary skill in the art will recognize that any other suitable material, such as fabrics, foams, plastics, and/or metals, can be used to form the structures and devices disclosed herein and that each of the structures and devices can be made from the same materials or from different materials or from any combination of materials.

As will be appreciated by those skilled in the art, any and all of the embodiments disclosed herein can be interchangeable with one another as needed. For example, an exemplary surgical access device kit could include multiple housings, cannulas, and actuation mechanisms. In any and all of the surgical access device embodiments disclosed herein, an engagement and/or release mechanism can be included to allow certain components of the surgical access device to be removable as needed. Any engagement and release mechanism known in the art, e.g., a snap-lock mechanism, corresponding threads, etc., can be used to releasably mate components of the device. Exemplary embodiments of an engagement and release mechanisms are described in more detail in U.S. patent application Ser. No. 12/242,765 entitled "Surgical Access Device" filed on Sep. 30, 2008, U.S. patent application Ser. No. 12/399,625 entitled "Methods and Devices for Providing Access to a Body Cavity" filed on Mar. 6, 2009, and U.S. patent application Ser. No. 12/399,482 entitled "Methods and Devices for Providing Access to a Body Cavity" filed on Mar. 6, 2009, and U.S. Pat. No. 7,371,227 entitled "Trocar Seal Assembly," issued May 13, 2008, and U.S. Pat. No. 5,628,732 entitled "Trocar With Improved Universal Seal," issued May 13, 2007, which are hereby incorporated by reference in their entireties.

There are various features that can optionally be included with any and all of the surgical access device embodiments disclosed herein. For example, a component of the device, such as a seal, housing, cannula, etc., can have one or more lights formed thereon or around a circumference thereof to enable better visualization when inserted within a patient. As will be appreciated, any wavelength of light can be used for various applications, whether visible or invisible. Any portion of the access device can also be opaque, semi-transparent, or optically clear. By way of non-limiting example, the distal tip of the obturator can be optically clear such that a scope inserted into a hollow obturator can provide visualization through the transparent tip. One of skill in the art will appreciate that the obturator tip can include one or more features to help penetrate tissue, e.g., tissue-separators, a tapered shape, a beveled edge (including a chamfered edge), a pointed needle, an electronic cutter, a sharp cutting blade, etc. By way of non-limiting example, the tip can include one or more tissue-separating wings which extend radially outward from the tip and converge to a lateral edge to assist in moving the tip through tissue and to help minimize damage to the tissue. Exemplary tip configurations are discussed in U.S. Patent Application No. 2007/0260121 entitled "Endoscopic Translumenal Surgical Systems," filed May 8, 2006, which is hereby incorporated by reference in its entirety. Any number of ports can also be included on and/or through the surgical access devices to enable the use of various surgical techniques and devices as needed in a particular procedure. For example, openings and ports can allow for the introduction of pressurized gases, vacuum systems, energy sources such as radiofrequency and ultrasound, irrigation, imaging, etc. As will be appreciated by those skilled in the art, any of these techniques and devices can be removably attachable to the surgical access device and can be exchanged and manipulated as needed.

Typically, during surgical procedures in a body cavity such as the abdomen, insufflation fluid is provided through an access device to expand the body cavity to facilitate the surgical procedure. Any and all of the surgical access devices described herein can also include various other features, such as one or more ventilation ports to allow evacuation of smoke during procedures that utilize cautery, and/or one or more insufflation ports through which the surgeon can insufflate the abdomen to cause pneumoperitenium, as described by way of non-limiting example in U.S. Patent Application No. 2006/0247673 entitled "Multi-port Laparoscopic Access Device" filed Nov. 2, 2006, which is hereby incorporated by reference in its entirety. The insufflation port can be located anywhere on the device, can have any size, and can accept a leur lock or a needle, as will be appreciated by those skilled in the art.

In order to maintain insufflation within the body cavity, the access devices disclosed herein can include at least one seal element. Various seal elements are known in the art, but typically the surgical access device can include at least one instrument seal that forms a seal around an instrument disposed therethrough, but otherwise does not form a seal when no instrument is disposed therethrough; at least one channel seal or zero-closure seal that seals the working channel created by the sealing port when no instrument is disposed therethrough; or a combination instrument seal and channel seal that is effective to both form a seal around an instrument disposed therethrough and to form a seal in the working channel when no instrument is disposed therethrough. A person skilled in the art will appreciate that various seals known in the art can be used including, e.g., duckbill seals, cone seals, flapper valves, gel seals, diaphragm seals, lip seals, iris seals, etc. A person skilled in the art will also appreciate that any combination of seals can be included in any of the embodiments described herein, whether or not the seal combinations are specifically discussed in the corresponding description of a particular embodiment. Seal elements can be disposed at various locations within the access devices described herein, by way of non-limiting example, positioned within sealing ports formed in the housing and/or the cannula. Seal elements can be formed integrally with the housing or cannula or can be selectively coupled thereto using a variety of means known in the art. The seal elements can be fixed relative to the housing and/or cannula or can be rotatable or movable. The seal elements used in the surgical access device can also be removable, replaceable, and interchangeable. Exemplary instrument seal configurations are described in more detail in U.S. patent application Ser. No. 12/399,482 entitled "Methods And Devices For Providing Access Into A Body Cavity," filed Mar. 6, 2009, U.S. Patent Publication No. 2004/0230161 entitled "Trocar Seal Assembly," filed on Mar. 31, 2004, and U.S. Patent Publication No. 2007/0185453 entitled "Conical Trocar Seal," filed on Oct. 15, 2003, which are hereby incorporated by reference in their entireties. Zero-closure seals can also include various other features, as described in more detail in U.S. Patent Publication No. 2009/0005799, entitled "Duckbill Seal with Fluid Drainage Feature," filed on Jun. 29, 2007, and U.S. Pat. No. 5,330,437, entitled "Self Sealing Flexible Elastomeric Valve and Trocar Assembly for Incorporating Same," filed Nov. 12, 1993, which are hereby incorporated by reference in their entirety.

Any and all embodiments of a surgical access device can also include one or more safety shields positioned through, in, and around any of the components and/or tissue to protect the components against puncture or tear by surgical instruments being inserted through the device. Exemplary embodiments of safety shields are described in more detail in U.S. Patent Publication No. 2006/0247673 entitled "Multi-port Laparoscopic Access Device" filed Nov. 2, 2006, U.S. patent application Ser. No. 12/399,625 entitled "Methods and Devices for Providing Access to a Body Cavity" filed on Mar. 6, 2009, U.S. patent application Ser. No. 12/399,482 entitled "Methods and Devices for Providing Access to a Body Cavity" filed on Mar. 6, 2009, and U.S. patent application Ser. No. 12/242,765 entitled "Surgical Access Device" filed on Sep. 30, 2008, which are hereby incorporated by reference in their entireties. Exemplary embodiments of various seal protectors are described in more detail in U.S. Pat. No. 5,342,315 entitled "Trocar Seal/Protector Assemblies," issued Aug. 30, 1994 and U.S. Pat. No. 7,163,525 entitled "Duckbill Seal Protector," issued Jan. 16, 2007, which are hereby incorporated by reference in their entireties.

A person skilled in the art will appreciate that, while methods and devices are described herein in connection with minimally invasive laparoscopic procedures in the abdominal cavity, the methods and devices can be used in almost any part of a human or animal body in any known and subsequently developed surgical procedures and methods. For example, any of the embodiments described herein can be used in performing a sleeve gastrectomy and/or a gastroplasty, as described in U.S. application Ser. No. 12/242,765 entitled "Surgical Access Device" filed on Sep. 30, 2008; U.S. application Ser. No. 12/242,711 entitled "Surgical Access Device with Protective Element" filed on Sep. 30, 2008; U.S. application Ser. No. 12/242,721 entitled "Multiple Port Surgical Access Device" filed on Sep. 30, 2008; U.S. application Ser. No. 12/242,726 entitled "Variable Surgical Access Device" filed on Sep. 30, 2008; U.S. application Ser. No. 12/242,333 entitled "Methods and Devices for Performing Gastrectomies and Gastroplasties" filed on Sep. 30, 2008; U.S. application Ser. No. 12/242,353 entitled "Methods and Devices for Performing Gastrectomies and Gastroplasties" filed on Sep. 30, 2008; and U.S. application Ser. No. 12/242,381 entitled "Methods and Devices for Performing Gastroplasties Using a Multiple Port Access Device" filed on Sep. 30, 2008, all of which are hereby incorporated by reference in their entireties.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., seal, housing, cannula, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. This can be done by any number of ways known to those skilled in the art including beta or gamma radiation, ethylene oxide, steam, and a liquid bath (e.g., cold soak). In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical access device, comprising:
   a housing;
   a cannula extending distally from the housing, the cannula and the housing defining a working channel extending longitudinally therethrough, the cannula being movable between an insertion configuration and a deployed configuration, and the cannula having a distal anchoring element having a maximum outer diameter in the deployed configuration that is greater than a maximum outer diameter of the cannula in the insertion configuration; and
   an obturator insertable through the working channel, the obturator having an engagement feature configured to mate with a complementary engagement feature formed on the cannula such that rotation of the obturator is effective to cause corresponding rotation of the cannula; and
   a head formed on a proximal end of the obturator and effective to change a length of the cannula extending between the housing and the anchoring element.

2. The surgical access device of claim 1, wherein the obturator is configured to move proximally relative to a proximal end of the cannula when the engagement features are engaged to move the cannula from the insertion configuration to the deployed configuration.

3. The surgical access device of claim 1, wherein the engagement features are formed on a distal end of the obturator and cannula.

4. The surgical access device of claim 1, wherein axial movement of the obturator within the cannula is effective to change a distance between the distal end of the cannula and a proximal end of the cannula.

5. The surgical access device of claim 1, wherein rotation of the obturator relative to the cannula is effective to cause the engagement features to engage with and disengage from one another.

6. The surgical access device of claim 1, wherein the engagement features comprise a protrusion extending from one of the cannula and the obturator and an opening formed in another one of the cannula and the obturator, the opening being configured to receive the protrusion.

7. The surgical access device of claim 1, further comprising an actuation mechanism formed on the obturator and effective to change a length of the obturator extending distal to the housing, and wherein changing the length of the obturator is effective to move the cannula between the insertion configuration and the deployed configuration.

8. The surgical access device of claim 1, wherein the cannula includes an elastically deformable and extendible outer sheath and first and second telescoping inner tubes.

9. The surgical access device of claim 1, further comprising at least one seal element disposed within the working channel and configured to form at least one of a seal around an instrument disposed through the working channel and a seal across the working channel when no instrument is disposed therethrough.

10. A surgical access device, comprising:
    a housing;
    a cannula extending distally from the housing, the cannula and the housing defining a working channel extending therethrough, and the cannula having an expandable anchor formed on a distal portion thereof;
    an obturator disposable within the working channel;
    a head formed on a proximal end of the obturator and effective to change a length of the cannula extending between the housing and the anchoring element; and
    a rotatable actuation mechanism operatively associated with the obturator and effective to expand the expandable anchor on the distal portion of the cannula when the obturator is fully disposed within the cannula such that a distal tip of the obturator extends beyond a distal end of the cannula.

11. The surgical access device of claim 10, wherein the rotatable actuation mechanism comprises a rotatable knob coupled to the obturator and effective to rotate to change a length of the obturator extending distal to the housing.

12. The surgical access device of claim 11, wherein the obturator has inner and outer tubes that are axially movable relative to one another, and wherein rotation of the rotatable knob is effective to move the inner tube relative to the outer tube.

13. The surgical access device of claim 12, wherein one of the inner and outer tubes includes a guide channel formed therein, and the other one of the inner and outer tubes includes a detent formed therein and slidably disposed within the guide channel, the guide channel and detent causing axial movement of the inner tube relative to the outer tube upon rotation of the rotatable knob.

14. The surgical access device of claim 12, wherein a distal end of the inner tube is configured to engage a distal end of the expandable anchor, and a distal end of the outer tube is configured to engage a proximal end of the expandable anchor.

15. The surgical access device of 10, wherein the expandable anchor is configured to expand upon movement of a distal end of the expandable anchor toward a proximal end of the expandable anchor.

16. The surgical access device of claim 15, wherein the obturator is configured to engage the proximal and distal ends of the expandable anchor and to move the proximal and distal ends of the expandable anchor toward one another to expand the expandable anchor.

17. The surgical access device of claim 10, wherein the obturator includes an keying element feature formed on a distal end thereof and configured to mate with a complementary keying element formed on a distal end of the cannula such that rotation of the obturator is effective to cause corresponding rotation of the cannula.

18. A surgical access device, comprising:
a housing;
a cannula extending distally from the housing, the cannula and the housing defining a working channel extending therethrough, and the cannula having an expandable anchor formed on a distal end thereof and movable between an insertion configuration and an expanded deployed configuration;
an obturator insertable through the working channel, the obturator being configured to move the expandable anchor between the insertion and deployed configurations, and the obturator being configured to selectively mate with the cannula such that rotation of the obturator is effective to cause corresponding rotation of the cannula; and
a head formed on a proximal end of the obturator and effective to change a length of the cannula extending between the housing and the anchoring element.

19. The surgical access device of claim 18, further comprising a rotatable member coupled to the obturator, wherein rotation of the rotatable member is effective to cause the obturator to move the expandable anchor between the insertion and deployed configurations.

* * * * *